United States Patent [19]

Hale et al.

[11] 4,325,797

[45] Apr. 20, 1982

[54] MEMBRANE MOUNTING METHOD AND MEMBRANE-ENCLOSED AMPEROMETRIC CELL

[75] Inventors: John M. Hale, Meinier; Eugen Weber, Hinwil, both of Switzerland

[73] Assignee: Orbisphere Corporation Wilmington, Succursale de Collonge-Bellerive, Collonge-Bellerive, Switzerland

[21] Appl. No.: 164,291

[22] Filed: Jun. 30, 1980

[51] Int. Cl.³ .............................................. G01N 27/30
[52] U.S. Cl. ................................. 204/195 P; 29/235; 29/592 R
[58] Field of Search ........................ 204/195 P, 1 P; 128/635; 29/592

[56] References Cited

U.S. PATENT DOCUMENTS 3,259,124  7/1966  Hillier et al. ................ 204/195 P X
3,835,014  9/1974  Huffhines ....................... 204/195 P

*Primary Examiner*—G. L. Kaplan
*Attorney, Agent, or Firm*—Werner W. Kleeman

[57] ABSTRACT

A method of mounting and securing a membrane of polymer film on an amperometric cell that has a cylindrical cell end provided with an electrolyte-bearing sensor face; the holding member is a substantially non-resilient and creep-resistant die ring, having a cylindrical inner surface that fits onto the cylindrical cell end; at least one tapered inner surface portion extends outwardly toward a leading end of the die ring; the leading end is moved over the cell end whereby the polymer film is deep-drawn between the die ring and the cylindrical cell end and is permanently shaped to form a cup-shaped membrane portion sealingly held by the die ring on the cylindrical cell end during operation of the amperometric cell.

An amperometric cell having a cylindrical cell end frontally provided with sensor face, a membrane formed of a flexible polymer film and extending over the sensor face; the membrane is in contact with the cylindrical cell end; a holding member is arranged around the membrane; the holding member is a non-resilient and creep-resistant die ring having a cylindrical inner surface fitting onto the cylindrical cell end and at least one tapered inner surface portion outwardly extending toward a leading end of the die ring; the membrane has a permanently formed cup-shaped portion sealingly held by the die ring on the cylindrical cell end during operation; the die ring can be removed, e.g., for cell maintenance and reused for applying and shaping a fresh membrane.

31 Claims, 5 Drawing Figures

MEMBRANE MOUNTING METHOD AND MEMBRANE-ENCLOSED AMPEROMETRIC CELL

CROSS-REFERENCE TO RELATED CASE

This application generally relates to subject matter disclosed in our commonly assigned U.S. application Ser. No. 773,163 filed Mar. 1, 1977, issued as U.S. Pat. No. 4,096,047 on June 20, 1978.

BACKGROUND OF THE INVENTION (a) Field of the Invention

This invention relates generally to the art of amperometric or polarographic measurement and amperometric or polarographic measuring devices of the type used for quantitative electrochemical analysis methods where the concentration of an electroactive species such as oxygen dissolved in or admixed with a fluid such as a gaseous or liquid medium is to be measured or monitored; more particularly, this invention relates to membrane-enclosed amperometric or polarographic cells and to methods of mounting and securing the membrane constituent on such cells.

(b) Description of the Prior Art

Electrochemical cells or transducers of the type used for quantitative electrochemical analysis are well known in the art and generally include a working or sensing electrode having a defined or electroanalytically effective surface, a counter electrode, an electrolyte in contact with the electrodes, a barrier means that is substantially impervious to the electrolyte but is permeable to a gas (i.e. a "semi-permeable membrane") and a cell structure or housing for receiving and holding the cell constituents in operative connection.

For amperometric analytical operation, the working electrode in a transducer-type cell arrangement is polarized by a constant DC voltage to furnish a current whose steady state magnitude is proportional to the activity of the chemical substance of interest. Transducers of this type and their operation and uses are discussed in detail in the following illustrative U.S. Pat. Nos. 2,913,386, 3,071,530, 3,223,608, 3,227,643, 3,372,103, 3,406,109, 3,429,796, 3,515,658 and 3,622,488.

The first mentioned U.S. Pat. No. 2,913,386 to Leland E. Clarke considered as the pioneering patent in this art already teaches a barrier means in the form of a semi-permeable membrane formed of a flexible polymer such as polyethylene and the terms "membrane-covered" or "membrane-enclosed" are being used generally to refer to such electroanalytical devices, e.g. as "membrane-covered polarographic detectors."

As the term "polarography" has also been used for techniques based on the dropping mercury electrode and operating either in a voltametric or galvanic mode, the term "membrane-enclosed amperometric cell" or MEAC is used herein to refer to electroanalytical devices of interest here such as the "Clark Cell" and modifications thereof.

A structural feature common to most prior art MEAC's is a generally cylindrical outer structure of the cell, e.g. provided by an elongated tubular cell housing or jacket that receives and holds the above mentioned cell components; as the electroanalytically effective surface of the sensing electrode is the site where the measuring signal is generated, and as this surface must be covered by an electrolyte layer formed between the membrane and the surface of the sensing electrode, the sensor face of a MEAC will generally be that cell portion where the electroactive species of interest can get through the membrane and the electrolyte layer on top of the sensing electrode surface to that electrode surface.

For convenience of construction as well as for structural and operative reasons, the sensor face of a MEAC generally is a front side of the cell structure, that is, generally vertically intersecting with the cell axis. As will be explained below in more detail, the frontal or "transversely" extending sensor face of a MEAC can be plane or curved ("calotte-shaped") and both types are known in the art.

As is also known in the art, a convenient method of securing a polymer membrane on the electrolyte-bearing sensor face of a MEAC is to use an annular holding member that presses a peripheral portion of a substantially circular polymer film onto the cylindrical end of the MEAC adjacent or near the sensor face.

For example, Clark in U.S. Pat. No. 2,913,386 discloses a cap-type holding member that presses an O-ring seal against the membrane and the cylindrical outer wall of the cell housing. Because one of the most frequent operations in the maintenance of a MEAC is exchange of the electrolyte and as this involves removal and replacing of the membrane, several modifications of the membrane-mounting and holding structure and method disclosed by Clark have been suggested and tried, cf. the elastic tubular holding member or the elastic O-ring sealingly retaining the stretched membrane in a cylindrical outer cell wall portion as disclosed by D. A. Okun et al. in U.S. Pat. No. 3,227,643, the disc-clamping device disclosed by J. A. Porter et al. in U.S. Pat. No. 3,445,369 and the membrane-holding cap assembly disclosed by T. M. Doniguian in U.S. Pat. No. 3,758,398.

Doniguian, after illustrating and explaining the disadvantages of prior art membrane mountings by means of an O-ring seal suggests incorporation of the membrane into a pre-assembled tubular cap for threading engagement with the cell housing. The periphery of the membrane is clamped and sealingly held between an internal bore of the cap and a tubular holding ring tightly fitting into the cap bore. For membrane mounting, the membrane/cap-assembly is supplied with electrolyte; then, the assembly is threaded onto the cell so that the calotte-shaped sensor face will forcibly stretch the membrane while retaining a thin film of electrolyte between the membrane and the sensing electrode.

An important further factor must be considered, however, when reviewing the problems of mounting a given semi-permeable membrane on a MEAC, i.e. the thickness or gauge of the membrane and its effect upon operation of a MEAC. For example, according to U.S. Pat. No. 3,227,643 a typical thickness of a polyethylene membrane is 1 mil (25 micrometers); a typical preferred thickness in the range of from 10 to 20 micrometers has been disclosed in our above mentioned U.S. Pat. No. 4,096,047 for high-tenacity polymers, such as polytetrafluoro ethylene, and membrane thicknesses of as low as 0.2 to 2 micrometers have been discussed in the literature (cf. M. L. Hitchman, Measurement of Dissolved Oxygen, ISBN 0471 03885-7; incorporated herein by way of reference); the main advantage of using thinner membranes is that the response time to step changes in the concentration of the measured species is decreased. An added advantage of relatively thin (i.e. up to 25 micrometers) membranes is that they can be mounted and secured on the cell by means of simple O-rings without substantial problems caused by wrinkling. On the other hand, the sensitivity of such thin membranes is substantial. For example, simply touching the normal membrane of a MEAC by hand can cause a change in membrane stress that can necessitate recalibration. Further, any comparatively rough treatment, such as brushing away an algae layer from such a thin membrane, may cause irreparable membrane damage.

When attempting to use relatively thicker membranes—for example when minimum response time to step change is less important than membrane stability—prior art membrane-mounting methods are not suitable; either—e.g. in the case of conventional O-ring seals—the problem of wrinkling or folding of the membrane at or near the sensor face and/or lack of sealing cannot be resolved or—e.g. with membrane/cap-assemblies—the stress of the membrane may cause time-dependent permeability changes aside from the relatively complicated and bulky structure of prior art membrane assemblies.

OBJECTS OF THE INVENTION

Thus, it is a primary object of the invention to provide an improved method of mounting and securing a membrane on a membrane-enclosed amperometric cell.

Another main object of the invention is a membrane-enclosed amperometric cell with an improved holding member and an improved shape of the membrane.

Still another object of the invention is a means to shapingly deform a semi-permeable membrane so as to improve mechanical and operational stability thereof.

Yet a further object of the invention is a novel holding member for the membrane of a membrane-enclosed amperometric cell which member is capable of shaping the membrane in a predetermined manner when the membrane is mounted on the cell.

Further objects will become apparent as this specification proceeds.

SUMMARY OF THE INVENTION

According to the present invention we have found that these objects will be achieved in the method of mounting and securing a membrane formed of a flexible polymer film on an amperometric cell having a substantially cylindrical cell end frontally provided with an electrolyte-bearing sensor face by means of a removable annular holding member, by using, as said holding member, a substantially non-resilient and creep-resistant die ring having a cylindrical inner surface slidingly fitting onto the cylindrical cell end and at least one tapered inner surface portion outwardly extending from the cylindrical inner surface toward a leading end portion of the die ring, and moving the leading end portion of the die ring over a predetermined length of the cylindrical cell end for deep-drawingly shaping the polymer film between the die ring and the cylindrical cell end and irreversibly forming a cup-shaped membrane portion extending over the electrolyte-bearing sensor face and an adjacent portion of the cylindrical cell end, the cup-shaped membrane portion being sealingly held by the die ring on the cylindrical cell end during operation of the amperometric cell.

In general, the invention is applicable to any membrane-enclosed amperometric cell which has a substantially cylindrical cell end frontally provided with an electrolyte-bearing sensor face that is to carry a membrane formed of a flexible polymer film extending over the sensor face and having a circumferential portion in contact with the cylindrical cell end and a removable annular holding member around said circumferential portion of the membrane for sealingly pressing the circumferential portion of the membrane onto said cell end, when the annular holding member is a substantially non-resilient and creep-resistant die ring having a cylindrical inner surface slidingly fitting onto said cylindrical cell end and at least one tapered inner surface portion outwardly extending from the cylindrical inner surface toward a leading end portion of the die ring; as a consequence of using such a die ring when applying the flexible polymer film, the membrane has a permanently formed cup-shaped portion extending over the electrolyte-bearing sensor face and an adjacent portion of the cylindrical cell end; further the cup-shaped membrane portion is sealingly held by the die ring on the cylindrical cell end during operation of the amperometric cell.

BRIEF DISCUSSION OF PREFERRED EMBODIMENTS OF THE INVENTION

In general, we prefer that the die ring has a symmetrical structure in a plane vertical to its axis, i.e. has two tapered inner surface portions each of which extends in a conical manner from the cylindrical inner die ring surface towards the adjacent end of the die ring so that either end can be used as the leading end for shapingly deforming the membrane.

By the term "substantially non-resilient" as applied to the die ring we understand a ring made of a material that has a modulus of elasticity ($M_E$) of at least about $2 \cdot 10^9$ Pascal (Pa), preferably at least about $1 \cdot 10^{10}$ Pa. The upper limit of the modulus of elasticity of the die ring material is not believed to be critical; a generally suitable range of the $M_E$ is from about $2 \cdot 10^9$ Pa to about $2 \cdot 10^{12}$ Pa. A suitable method of determining the $M_E$ of a given material is defined in ASTM D 638-61T. As the Pascal Unit (defined as Newton per square meter) has been introduced but recently, conversion of previously used units may be required, e.g. from $dyn/cm^2$ units in which the above $M_E$ range would extend from $2 \cdot 10^{10}$ to $2000 \cdot 10^{10}$ $dyn/cm^2$.

Further, it should be noted that the $M_E$ can also be designated as "tensile modulus" or "Young's Modulus" and that numerical values of these modulae are substantially the same for a given material.

While the die ring could be made of a non-resilient, high yield strength polymer material, such as polyacetals, polycarbonates, polysulfones, polyphenylene oxides, poly-(styrene acrylonitrile) and poly-(acrylonitrile butadiene styrene), notably if reinforced with glass fibers, carbon fibers, or the like, we generally prefer a die ring made of a substantially inert structural metal, such as stainless steel, that has an $M_E$ in the order of $10^{11}$ Pa, e.g. about $2 \cdot 10^{11}$ Pa.

The term "substantially inert" as applied to the material of the die ring is used herein to describe a material that is chemically inert against the electrolytes used in the cell and against all normal ambient conditions encountered in use of the cell.

In addition to being substantially non-resilient as evidenced by the above mentioned Pascal range, the die ring must be substantially creep-resistant. In general, the creep modulus ($M_C$) of the material of the die ring should be at least $1.35 \cdot 10^8$ Pa, preferably at least $2.7 \cdot 10^9$ Pa. The above examples generally satisfy this condition and again metals, such as stainless steel, are preferred over organic polymers in view of better creep resistance. A suitable method for determining the $M_C$ of a candidate material is defined in ASTM D 790-63. In general, the temperature of measurement of both $M_E$ and $M_C$ should be commensurate with the ambient temperatures when using the cell, i.e. in the broadest range of from minus 30° to 200° C. and specifically the normal temperature range of from minus 10° to 100° C. Further, as the $M_C$ may be regarded as a time-dependent parameter, the $M_C$ values should be commensurate with the normal operating life of the die ring, e.g. $10^2$ to $10^4$ hours depending somewhat upon the specific type of cell, the intended use thereof and the recommended cell maintenance provisions.

A die ring preferred for many purposes of the invention is defined by a substantially cylindrical outer surface extending between a pair of annular front end faces—both of which can serve as the leading end—and by an inner surface consisting of the cylindrical inner surface and two tapered surface portions, each of which extends from one end of the cylindrical inner surface portion to the adjacent annular top (or bottom) end face of the die ring. One of the annular end faces serves as the leading end of the die ring and comes to bear against a stop means on the cell, e.g. a rim or shoulder, arranged to limit axial movement of the die ring relative to the cell when deep-drawing the membrane; the other annular end face of the die ring will serve as a contact surface receiving the mechanical pressure applied for effecting the die ring movement when mounting and deep-drawing the membrane.

For many purposes it is preferred that the axial length of each of the tapered inner surface portions of the die ring is at least equal to the axial length of the cylindrical inner surface of the die ring. The total axial length of the die ring may depend upon the cell structure; for many purposes a total axial length of the ring in the range of from 2 to 10 mm, preferably 3 to 5 mm, will be satisfactory for an outer diameter of the ring die in the range of from 15 to 30 mm, preferably from 20 to 30 mm. Typically, the difference between the outer diameter and the inner diameter of the ring (measured as the distance between radially opposed points on the cylindrical inner die ring surface) is in the order of 10%. The axial length of the cylindrical inner surface portion of the die ring typically is in the range of from 5 to 40%, preferably 10 to 30% of the total axial length of the ring. The inner diameter of the die ring depends upon the outer diameter of the cylindrical cell end as the die ring should slidingly fit thereon. In this context, "slidingly fitting" is an operational term intended to express the requirement that for membrane mounting and membrane shaping the die ring is to be moved over a portion of the outer surface of the cell end which is adjacent to the sensor face with the polymer film thereon.

Generally depending on the thickness of the polymer film and its deep-drawing (i.e. cold-flow deformation) characteristics, the inner diameter (as defined above) of the die ring will be somewhat greater than the outer diameter of the cylindrical cell end next to the sensor face. For example, such difference will correspond to about 1 to 2 times the thickness of the polymer film.

As mentioned above, relatively thick membranes may be desirable for cell operation in view of maximum stability. For example, polymer films having a thickness in the range of from about 25 micrometers ($\mu$m) to about 700 $\mu$m may be used advantageously for the purposes of the invention and a membrane thickness range of from about 50 $\mu$m to about 300 $\mu$m is particularly preferred. Highly stable MEAC's according to the invention may be obtained with a membrane thickness of 100 $\mu$m when using preferred polyfluoro ethylene films in "as cast" condition for forming the membrane.

As is known in the polymer art, a given polymer film of the type suitable for semi-permeable membranes may have substantial cold-flow characteristics depending its degree of molecular orientation. In the "as cast" condition such a polymer film may be stretched monoaxially or biaxially by several times the length before stretching.

Most elastomeric and thermoset (cross-linked) polymers cannot be permanently stretched by cold-flow and are not preferred for the invention. Thus, polymers suitable for use in the invention are "thermoplastic" in the sense of consisting of substantially linear polymer chains with no or very little interchain cross-linking and the polymer chains in "as cast" condition will be "coiled" to some extent as evidenced by a substantial cold-stretching capacity of a film of the polymer.

While not wishing to be bound by any specific theory, it may be assumed that an increasing molecular orientation of a given thermoplastic polymer film, e.g. by stretching, will increase its mechanical strength and decrease its permeability to gases. Ideally, a semi-permeable membrane of a MEAC should have maximum permeability for the gaseous constituent to be measured, e.g. oxygen, adjacent the sensing electrode (at or near center of sensor face) and optimal strength for the membrane holding mechanism.

It is believed that the die ring used according to the invention provides for a membrane with a minimum of, or substantially no stretch-induced orientation, and, hence, maximum gas permeability adjacent the sensing electrode and significant stretch-induced orientation and, hence, maximum strength at the sealing interface between the annular holding member and the cylindrical cell end.

The effect that stretch-induced orientation of the membrane is effected between the inventive die ring and the cell end but not, or to a substantially lesser extent, on top of the sensor face is evidenced by the fact that an "as cast" and substantially flat polymer film will be permanently shaped by the die ring (working as a female die portion) in cooperation with the cell end plus frontal sensor face (working as a male die portion) to form a cup-shaped structure having its top portion on the sensor face of the cell and its cylindrical side portion between the adjacent cell end and the die ring when the latter is in its membrane-holding portion; the cylindrical side portion of the cup will have a smaller thickness than the "as cast" film while the top portion does not show a significant change of original film thickness.

To safely preclude unintentional stretching of the membrane on top of the sensor face we prefer to resiliently press the polymer film onto the electrolyte bearing sensor face during the deep-drawing operation caused by movement of the die ring over a predetermined end portion of the cylindrical outer cell surface, e.g. by means of a relatively soft rubber plate. This will be explained in more detail below.

BRIEF DESCRIPTION OF THE DRAWINGS

The invention will be better understood and objects other than those set forth above will become apparent when considering the following detailed description thereof. Such description makes reference to the annexed drawings, wherein.

DETAILED DESCRIPTION OF THE PREFERRED EMBODIMENTS

Figure 1:
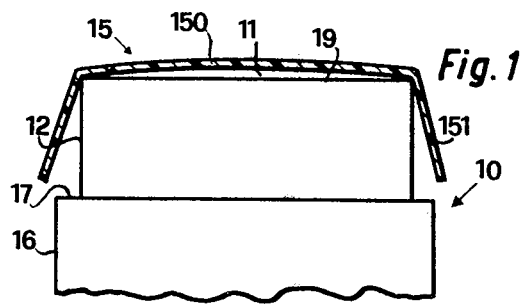
FIG. 1 is a simplified side view of the broken-away sensor end portion of an amperometric cell with a piece of polymer film, shown diagrammatically in section, layed on the sensor face.
Figure 2:
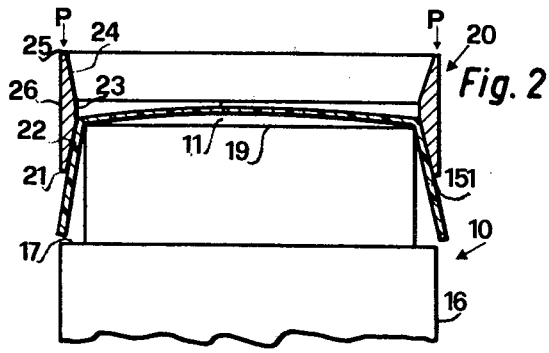
FIG. 2 is the side view shown in FIG. 1 plus the die ring, shown in section, at the start of its movement over the cylindrical cell end.
Figure 3:
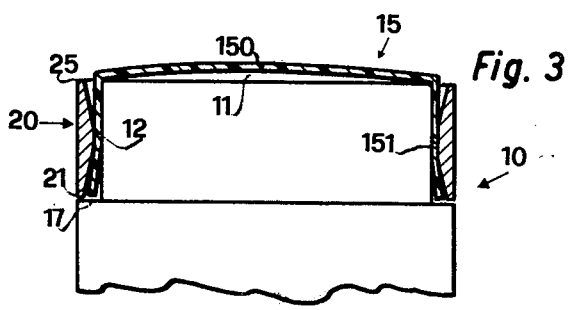
FIG. 3 is the side view shown in FIG. 1 with the die ring, shown in section, in its final position for operation of the membrane-enclosed amperometric cell.

FIGS. 1–3 illustrate the steps of the membrane-mounting and membrane-securing method of the invention:

First, a membrane blank, e.g. a substantially circular piece of a substantially flat polymer film 15 capable of cold-flow deformation (deep-drawing) is put on the sensor face 11 of cell 10.

Prior to applying membrane 15, the electrolyte-receiving portions or recesses (not shown) are filled to saturation in a conventional manner with an electrolyte. Sufficient electrolyte is provided so that a continuous film of electrolyte (not shown) is formed between sensor face 11 and polymer film 15.

It should be emphasized that the internal structure of cell 10 is not part of the subject invention as many cell structures are known in the art, e.g. as set forth in the above mentioned literature. As will be apparent to one experienced in the art of amperometric analysis, cell structure, electrolyte composition and cell operating conditions depend upon the electroactive species of interest and the intended type of measurement or monitoring including sensitivity.

Determination of oxygen in a gaseous or liquid medium is a preferred example, such as measurement of dissolved oxygen for the various purposes mentioned in the above quoted monography by M. L. Hitchman as well as the literature cited therein.

As an example of a cell structure suitable for oxygen determination in the sensitivity range extending from percents to parts per billion, the structure disclosed in our commonly assigned U.S. Pat. No. 4,096,047 is given but numerous other known cell structures can be used for the subject invention as well as long as the general cell structure is essentially coaxial in the sense that the sensor face is a frontal part of a generally cylindrical cell end.

Preferably, the sensing electrode surface (not shown) is a substantially coplanar constituent of sensor face 11 which, in turn, preferably is slightly convex and curved ("calotte-shaped"), i.e. defined by the surface of a sphere or spheroid having a radius in the range of typically from about 25 to about 250 mm.

Adjacent to sensor face 11 of cell 10 is the cylindrical cell end 12, e.g. formed in the outer side of the cell jacket or wall member 16. Conventionally, such jacket member 16 is generally made of an electrical insulator material, e.g. an organic polymer of the thermoplastic or thermoset ("duroplastic" or cross-linked) species. Such polymers having a compressive modulus (e.g. determined according to ASTM D 695-63T) of at least about $2 \cdot 10^9$ Pa are preferred for the invention, notably those having a creep modulus (as defined above) of at least about $1 \cdot 35 \cdot 10^8$ Pa. In addition to the specific non-resilient and creep-resistant polymers mentioned above for use in the die ring (where metal is preferred, however), other examples suitable for cell wall member 16 include phenoplasts, aminoplasts and the like duroplastic material with or without conventional fillers. As is known per se, the material for outer cell wall member 16 should be substantially inert to ambient conditions of cell 10.

In general, the cylindrical cell end portion 12 is formed, e.g. by machining, as a recessed portion of jacket member 16 so as to form a stop means or shoulder 17 to limit movement of the die ring 20 as shown in FIGS. 2 and 3. Preferably, the radial width of shoulder 17 is substantially the same as the total radial thickness of ring 20. This is not a critical requirement but provides for general structural benefits of using cell 10, e.g. for introducing the sensing head into the neck of a bottle, flow chamber or the like.

The diameter of polymer film 15 is sufficient to provide for an overlap over sensor face 11, i.e. so that the peripheral end portion 151 of film 15 extends over the axial length of the cylindrical cell end portion 12 or at least a major portion thereof.

At the edge 19 between sensor face 11 and cell end 12, a relatively thin polymer film 15 will bend under its own weight forming a plurality of radially extending folds or wrinkles (not shown).

While a preferred method of applying die ring 20 while resiliently pressing top portion 150 onto electrolyte-bearing sensor face 11 will be explained below, it may be sufficient to gently press film top portion 150 by hand onto the electrolyte-bearing sensor face 11 so as to remove any air bubbles entrapped at the interface.

As shown in FIG. 2, die ring 20 is applied now. When leading end 21 of ring 20 is moved axially towards shoulder 17, the tapered inner surface 22 of ring 20 forces peripheral portion 151 of film 15 towards cylindrical end 12 of the cell and a number of radially extending folds (not shown) will be formed in film portion 151.

Now, a pressure P is applied as indicated in FIG. 2 by an arrow onto the rear end 25 of ring 20, preferably in a generally planar manner as by a plate (not shown). Then, the cylindrical inner surface portion 23 of ring 20 moves over edge 19 and begins to deep-drawingly deform film 15. The inner diameter of inner surface portion 23 will generally be slightly greater than the outer diameter of cylindrical cell end 12, e.g. by about 1 to 2 times the film thickness depending upon the deep-drawing characteristics of film 15 and the $M_E$ of the material of ring 20. When using a ring 20 of the less preferred polymer type ($M_E$ in the range of typically from about $2 \cdot 10_9$ to $1 \cdot 10^{10}$ Pa) the inner diameter of inner ring surface 23 may be substantially the same as the outer diameter of end 12, notably when using relatively thin films in the 10 to 25 μm range.

When using relatively thick films of more than 25 μm and preferably more than 50 μm, die ring 20 generally is made of a metal, such as stainless steel.

Movement of ring 20 by pressure P is continued until the leading end 21 of ring 20 comes to rest against shoulder 17 as shown in FIG. 3. This is the final operative position of ring 20 for use of cell 10. Polymer film 15 is now in the form of cup-shaped membrane structure with its top portion 150 pressed onto electrolyte-bearing sensor face 11 and its peripheral portion 151 firmly held between ring 20 and the outer surface of cell end 12. No air will be entrapped in sensitive interface portions, i.e. the interface between membrane 15 and the cell surface extending from the area of contact of inner ring surface 23 upwardly to and extending over sensor face 11.

As a rule, stretch-induced deformation of membrane 15 is substantially limited to the cylindrical side portions of the cup-shaped membrane structure obtained by deep-drawing extending from edge 19 downwards to inner ring surface 23. In that stretch-oriented portion of the peripheral film portion 151 the film thickness will be decreased while the yield strength will be increased.

The pressure P required for such deep-drawing of membranes depends somewhat on the thickness of the polymer film used and its deep-drawing characteristics. With preferred polymer films, such as polyfluoroalkanes (e.g. "Teflon", registered Trade Mark by E. I. Du Pont de Nemours and Company) in a thickness range of from about 10 to about 700 $\mu$m, preferably of from about 50 to about 300 $\mu$m, loads in the range of from about 1 to 20 kg will generally be sufficient.

For disassembly of the membrane-holding structure shown in FIG. 3, e.g. for exchanging electrolyte and membrane, the old membrane can be removed by gently levering of ring 20, e.g. with the finger nails or with a screw-driver. Examination of the removed membrane will show that the side wall portion extending from the top to the area of contact with surface 23 of ring 20 in the membrane-holding position of FIG. 3 is smooth and substantially free of folds or wrinkles.

Figure 4:
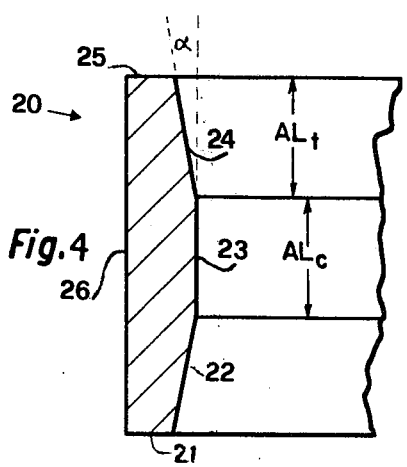
FIG. 4 is the enlarged cross-sectional view of a broken-away portion of the die ring of FIGS. 2 and 3.

FIG. 4 shows an enlarged cross-sectional view of the die ring 20 depicted in FIGS. 1–3. As will be understood on the basis of the above explanation of the function of ring 20 when deep-drawing film 15 and retaining the cup-shaped membrane obtained on cell 10, the tapered inner surface portion between the leading end and the cylindrical inner ring surface as well as that inner ring surface are essential for deep-drawing. Thus, when the frontal ring end face 21 is used as the leading end, tapered inner surface 22 is critical while tapered inner suface 24 is not and could be omitted.

For practical reasons, the die ring according to the invention is preferably mirror-symmetrical as viewed from a radial plane through the ring midway between its two annular ends 21, 25 so that it can be used with either end as the leading end for membrane shaping.

As an example, the actual dimensions of ring 20 are given for a cell having a sensor end substantially as shown in FIG. 1, the cylindrical end 12 having an outer diameter of 23.0 mm, an axial length of 4 mm and wherein the outer diameter of cylindrical cell portion 16 is 25 mm. For such a cell a die ring 20 made of commercial stainless steel (grade 316), e.g. by machining from a cylindrical rod, will be satisfactory for shaping and securing membranes of commercial "Teflon" polymer film having a thickness of 100 $\mu$m when die ring 20 has the following dimensions (FIG. 4): axial length of outer cylindrical ring surface 26 is 4 mm, diameter of inner cylindrical ring surface 23 is 22.8 mm, axial length of surface 23 is 1 mm, radial width of annular ends 21, 25 is 1.1 mm and outer ring diameter is 25 mm.

Generally, relatively small tapering angles ($\alpha$ in FIG. 4) in the range of from about 2° to about 10° will be satisfactory for many purposes of the invention.

The axial length of the upper tapered portion 24 is shown in FIG. 4 as $AL_t$ and the axial length of the cylindrical portion 23 is shown as $AL_c$. The length $AL_t$ may be at least equal to the length $AL_c$.

Figure 5:
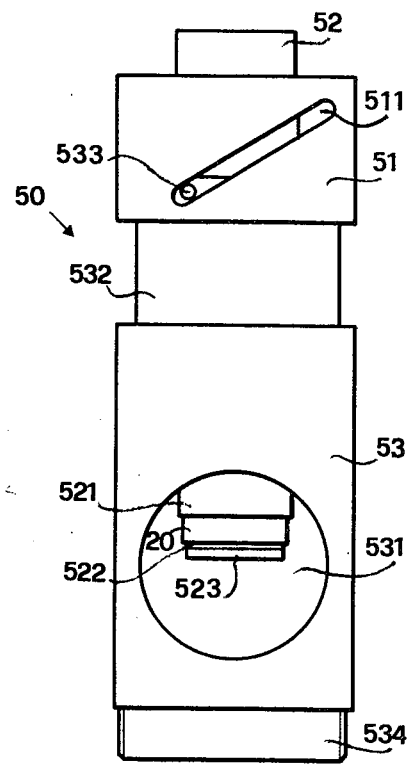
FIG. 5 is a simplified side view of an applicator device for membrane-mounting using a die ring, and of a broken-away portion of a sensor supported by a collar, shown in section, for engagement with the applicator device.
Figure 5:
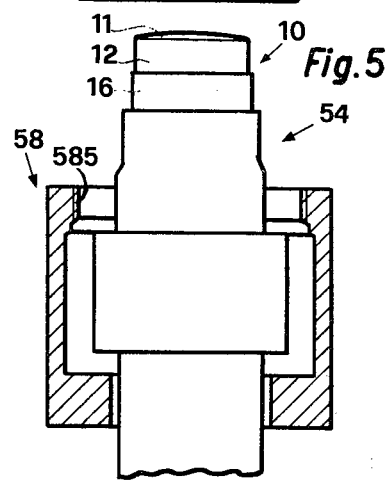

FIG. 5 illustrates an applicator or membrane mounting device 50 for use in the inventive method. It comprises a plunger 52 extending through cam 51 and a central bore (not shown) in outer cylinder 53 into the opening 531 of cylinder 53. Plunger 52 is made of two movable coaxial tubular members having lower ends 521 and 522 extending into opening 531 and an intermediate spring (not shown). The top of plunger 52 is rotatably connected with cam 51 which has a guide slot 511 for guiding pin 533 that is screwed into cam guide portion 532 of outer cylinder 53.

The lower end of inner tubular member 522 of plunger 52 temporarily carries a die ring 20 and has an end plate 523 made of rubber. When actuating plunger 52 by turning cam 51, both tubular members 521, 522 will move together; however, when end plate 523 during downward movement of plunger 52 comes into engagement with a stop-face and plunger actuation is continued, the spring between tubular members 521, 522 will be compressed and exert a growing pressure via plate 523 against the stop-face; at the same time, downward movement of outer tubular member 521 continues so that ring 20 will be pushed down from inner tubular member 522 and over end plate 523.

The lower end of cylinder 53 is provided with a thread portion 534 for engagement with a corresponding thread portion 585 of collar 58. Collar 58 receives and supports amperometric cell 54 with a sensor end portion 10 as explained in FIG. 1 (minus polymer film 15) and including frontal sensor face 11, cylindrical cell end 12 and cell wall member 16.

Operation of device 50 (FIG. 5) according to the invention for mounting and securing a membrane on the sensor end portion 10 of amperometric device 54 will now be explained in a step-by-step manner:

(1) Fill sensor via face 11 with electrolyte until a convex meniscus is visible above the profile of face 11; eliminate bubbles by tapping the side;

(2) push die ring 20 on to the lower end of plunger tube 522 sufficiently firmly that it cannot fall off; check that the rubber face 523 which contacts the membrane (not shown) is clean;

(3) raise plunger 52 to its uppermost limit by turning cam 51 at the top of plunger 52 in the anticlockwise direction;

(4) attach membrane mounting device 50 to sensor 54 by means of collar 38;

(5) place a clean disc of polymer film for the membrane (not shown) on sensor face 11 in a centrally symmetrical position;

(6) lower plunger 52 slowly by turning cam 51; pause for a few seconds when rubber end 523 of plunger 52 is pressed lightly on to the polymer film to allow excess electrolyte to escape from the top of sensor 54; then continue turning cam 51 to its limit to force die ring 20 from its temporary position on 522 into its final position on cylindrical cell end 12 of sensor 54;

(7) unscrew cam 51 to raise plunger 52 and detach membrane mounting device 50 from collar 58; best performance of sensor 54 is achieved if the membrane-enclosed end is completely free of air bubbles and the membrane is free of folds or wrinkles;

(8) wash excess electrolyte off the outside of the sensor and wipe dry.

While use of an applicator of the type illustrated in FIG. 5 is not critical, such use embodies a most convenient and preferred way of operating the inventive method.

Suitable modifications could be made to the system described here without departing from the inventive concept of a die ring for mounting, shaping and holding a membrane on an amperometric cell. So, while certain preferred embodiments of the invention have been explained in some detail for illustration, it is to be understood that the invention is not limited thereto but may be otherwise embodied and practiced within the scope of the following claims.

What is claimed is:

1. In the method of mounting and securing a membrane formed of a flexible polymer film on an amperometric cell having a substantially cylindrical cell end frontally provided with an electrolyte-bearing sensor face by means of a removable annular holding member; the improvement consisting of using as said holding member a substantially non-resilient and creep-resistant die ring having (a) a cylindrical inner surface slidingly fitting onto said cylindrical cell end and (b) at least one tapered inner surface portion outwardly extending from said cylindrical inner surface toward a leading end portion of said die ring; moving said leading end portion of said die ring over a predetermined length of said cylindrical cell end for deep-drawingly shaping said polymer film between said die ring and said cylindrical cell end and irreversibly forming a cup-shaped membrane portion extending over said electrolyte-bearing sensor face and an adjacent portion of said cylindrical cell end, said cup-shaped membrane portion being sealingly held by said die ring on said cylindrical cell end during operation of said amperometric cell.

2. The method of claim 1 wherein said die ring has two tapered inner surface portions each extending outwardly from said cylindrical inner surface toward an end portion of said die ring.

3. The method of claim 2 wherein said die ring is defined by a substantially cylindrical outer surface extending between a pair of annular front end faces, and by an inner surface consisting of said cylindrical inner surface and said two tapered surface portions each of which extends from one end of said cylindrical inner surface portion to an adjacent annular top end face of said die ring.

4. The method of claim 1 wherein said die ring has a modulus of elasticity of at least about $2 \cdot 10^9$ Pa.

5. The method of claim 1 wherein said die ring has a creep modulus of at least $1 \cdot 35 \cdot 10^8$ Pa.

6. The method of claim 1 wherein said die ring is made of a substantially inert metal having a modulus of elasticity of at least about $1 \cdot 10^{10}$ Pa and a creep modulus of at least $2 \cdot 7 \cdot 10^9$ Pa.

7. The method of claim 1 wherein said die ring is made of stainless steel.

8. The method of claim 1 wherein the axial length of each of said tapered inner surface portions of said die ring is at least equal to the axial length of said cylindrical inner surface of said die ring.

9. The method of claim 1 wherein said polymer film has a thickness in the range of from about 25 $\mu$m to about 700 $\mu$m.

10. The method of claim 9 wherein said polymer film has a thickness in the range of from about 50 $\mu$m to about 300 $\mu$m.

11. The method of claim 1 wherein said membrane on said sensor face is substantially free of stretch-induced orientation while said polymer film held on said cylindrical cell end is stretch-oriented by said movement of said die ring in a portion extending substantially from the top of said cylindrical cell end to said cylindrical inner surface of said die ring.

12. The method of claim 1 wherein said cup-shaped membrane portion consists of a top wall portion where said polymer film is substantially free of stretch-induced orientation, and of an adjacent side wall portion where said polymer film is oriented by stretching.

13. The method of claim 12 wherein said cylindrical side wall portion is thinner than said top wall portion of said cup-shaped membrane portion.

14. The method of claim 1 comprising the additional step of resiliently pressing said membrane onto said electrolyte-bearing sensor face when said leading end portion of said die ring is moved over said predetermined length of said cylindrical cell end.

15. The method of claim 1 comprising providing a stop means on said cylindrical cell end for limiting said movement of said die ring when said polymer film is deep-drawn.

16. The method of claim 15 wherein said stop means is an annular shoulder on said cell end distanced from said sensor face by a length that is substantially the same as the axial length of said die ring.

17. In a membrane-enclosed amperometric cell having a substantially cylindrical cell end frontally provided with an electrolyte-bearing sensor face, a membrane formed of a flexible polymer film extending over said sensor face and having a circumferential portion in contact with said cylindrical cell end; and a removable annular holding member around said circumferential portion of said membrane for sealingly pressing said circumferential portion of said membrane onto said cell end; the improvement wherein said annular holding member is a substantially non-resilient and creep-resistant die ring having (a) a cylindrical inner surface slidingly fitting onto said cylindrical cell end and (b) at least one tapered inner surface portion outwardly extending from said cylindrical inner surface toward a leading end portion of said die ring; and wherein said membrane has a permanently formed cup-shaped portion extending over said electrolyte-bearing sensor face and an adjacent portion of said cylindrical cell end, said cup-shaped membrane portion being sealingly held by said die ring on said cylindrical cell end during operation of said amperometric cell.

18. The cell of claim 17 wherein said die ring has two conically tapered inner surface portions each extending outwardly from said cylindrical inner surface toward an end portion of said die ring.

19. The cell of claim 18 wherein said die ring is defined by a substantially cylindrical outer surface extending between a pair of annular front end faces, and by an inner surface consisting of said cylindrical inner surface and said two conically tapered surface portions each of which extends from one end of said cylindrical inner surface portion to an adjacent annular front end face of said die ring.

20. The cell of claim 17 wherein said die ring has a modulus of elasticity of at least about $2 \cdot 10^9$ Pa.

21. The cell of claim 17 wherein said die ring has a creep modulus of at least $1.35 \cdot 10^8$ Pa.

22. The cell of claim 17 wherein said die ring substantially consists of an inert metal having a modulus of elasticity of at least about $1 \cdot 10^{10}$ Pa and a creep modulus of at least $2.7 \cdot 10^9$ Pa.

23. The cell of claim 17 wherein said die ring substantially consists of stainless steel.

24. The cell of claim 17 wherein the axial length of each of said tapered inner surface portion of said die ring is at least equal to the axial length of said cylindrical inner surface of said die ring.

25. The cell of claim 17 wherein said polymer film has a thickness in the range of from about 25 μm to about 700 μm.

26. The cell of claim 25 wherein said polymer film has a thickness in the range of from about 50 μm to about 300 μm.

27. The cell of claim 25 wherein said polymer film adjacent said sensor face is substantially free of stretch orientation while said polymer film adjacent said cylindrical cell end is stretch-oriented in a portion extending from the top of said cylindrical cell end to said cylindrical inner surface of said die ring.

28. The cell of claim 17 wherein said cup-shaped membrane portion consists of a top of wall portion where said polymer film is substantially free of stretch-induced orientation, and of a substantially cylindrical side wall portion where said polymer film is stretch-oriented, said side wall portion extending substantially from said top wall portion to said cylindrical inner surface of said die ring.

29. The cell of claim 28 wherein said cylindrical side wall portion is thinner than said top wall portion of said cup-shaped membrane portion.

30. The cell of claim 17 wherein said cylindrical cell end has a stop means for contact with said leading end of said die ring.

31. The cell of claim 30 wherein said stop means is an annular shoulder on said cell end distanced from said sensor face by a distance that is substantially the same as the axial length of said die ring.

* * * * *